(12) United States Patent
Bettuchi

(10) Patent No.: US 7,793,813 B2
(45) Date of Patent: Sep. 14, 2010

(54) HUB FOR POSITIONING ANNULAR STRUCTURE ON A SURGICAL DEVICE

(75) Inventor: Michael J. Bettuchi, Middletown, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 11/365,636

(22) Filed: Feb. 28, 2006

(65) Prior Publication Data

US 2007/0203509 A1      Aug. 30, 2007

(51) Int. Cl.
  *A61B 17/04*     (2006.01)
  *A61B 17/10*     (2006.01)
  *A61B 17/08*     (2006.01)
(52) U.S. Cl. .................................... 227/179.1; 606/153
(58) Field of Classification Search ......... 606/153–154, 606/213, 75, 151, 219, 232; 227/19, 179.1, 227/175.1, 180.1, 181.1
See application file for complete search history.

(56) References Cited

U.S. PATENT DOCUMENTS

| | | | |
|---|---|---|---|
| 3,054,406 A | 9/1962 | Usher | |
| 3,124,136 A | 3/1964 | Usher | |
| 4,347,847 A | 9/1982 | Usher | |
| 4,354,628 A | 10/1982 | Green | |
| 4,452,245 A | 6/1984 | Usher | |
| 4,605,730 A | 8/1986 | Shalaby et al. | |
| 4,655,221 A | 4/1987 | Devereux | |
| 4,834,090 A | 5/1989 | Moore | |
| 4,838,884 A | 6/1989 | Dumican et al. | |
| 4,930,674 A | 6/1990 | Barak | |
| 5,002,551 A | 3/1991 | Linsky et al. | |
| 5,014,899 A | 5/1991 | Presty et al. | |
| 5,040,715 A | 8/1991 | Green et al. | |
| 5,065,929 A | 11/1991 | Schulze et al. | |
| 5,205,459 A * | 4/1993 | Brinkerhoff et al. | 227/179.1 |
| 5,263,629 A | 11/1993 | Trumbull et al. | |
| 5,314,471 A | 5/1994 | Brauker et al. | |
| 5,344,454 A | 9/1994 | Clarke et al. | |
| 5,392,979 A | 2/1995 | Green et al. | |
| 5,397,324 A | 3/1995 | Carroll et al. | |
| 5,425,745 A | 6/1995 | Green et al. | |
| 5,441,193 A | 8/1995 | Gravener | |
| 5,441,507 A | 8/1995 | Wilk et al. | |
| 5,468,253 A | 11/1995 | Bezwada et al. | |
| 5,503,638 A | 4/1996 | Cooper et al. | |

(Continued)

FOREIGN PATENT DOCUMENTS

DE        199 24 311        11/2000

(Continued)

OTHER PUBLICATIONS

International Search Report from application EP 06016962.0 dated Jan. 3, 2007.

(Continued)

*Primary Examiner*—Todd E Manahan
*Assistant Examiner*—Lindsey Bachman

(57) ABSTRACT

An apparatus for forming an anastomosis between adjacent intestinal sections is provided. The apparatus includes an anastomosis device including an anvil assembly having a shaft which is selectively attachable to a tubular body portion; and a hub for locating an annular structure between the adjacent intestinal sections. The hub includes a central sleeve defining a lumen for receiving the shaft of the anvil assembly therein. The central sleeve forms a connection portion for engaging a feature on the anastomosis device and connecting the hub to the device. The apparatus further includes an annular structure operatively connected to the sleeve and extending radially outwardly therefrom.

7 Claims, 5 Drawing Sheets

U.S. PATENT DOCUMENTS

| | | |
|---|---|---|
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,415 A | 4/1999 | Tucke |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,676,671 B2 * | 1/2004 | Robertson et al. ........... 606/139 |
| 6,677,258 B2 | 1/2004 | Carroll et al. |
| 6,685,714 B2 | 2/2004 | Rousseau |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,927,315 B1 | 8/2005 | Heinecke et al. |
| 6,959,851 B2 * | 11/2005 | Heinrich ................. 227/175.1 |
| 7,128,748 B2 | 10/2006 | Mooradian et al. |
| 2002/0016626 A1 | 2/2002 | DiMatteo et al. |
| 2002/0019187 A1 | 2/2002 | Carroll et al. |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2003/0065345 A1 | 4/2003 | Weadock |
| 2003/0065346 A1 | 4/2003 | Evens et al. |
| 2003/0083676 A1 | 5/2003 | Wallace |
| 2003/0105510 A1 | 6/2003 | DiMatteo et al. |
| 2003/0114866 A1 | 6/2003 | Ulmsten et al. |
| 2003/0120284 A1 | 6/2003 | Palacios |
| 2003/0167064 A1 | 9/2003 | Whayne |
| 2003/0181927 A1 | 9/2003 | Wallace |
| 2003/0183671 A1 | 10/2003 | Mooradian et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 * | 3/2005 | Bauman et al. ............. 606/215 |
| 2005/0059997 A1 | 3/2005 | Bauman et al. |
| 2005/0080437 A1 * | 4/2005 | Wright ....................... 606/153 |
| 2005/0118435 A1 | 6/2005 | DeLucia et al. |
| 2005/0228446 A1 * | 10/2005 | Mooradian et al. .......... 606/215 |
| 2006/0004407 A1 | 1/2006 | Hiles et al. |
| 2006/0085034 A1 * | 4/2006 | Bettuchi .................... 606/219 |
| 2006/0135992 A1 * | 6/2006 | Bettuchi et al. ............. 606/219 |
| 2006/0173470 A1 | 8/2006 | Oray et al. |
| 2006/0178683 A1 | 8/2006 | Shimoji et al. |
| 2006/0212050 A1 | 9/2006 | D'Agostino et al. |
| 2006/0271104 A1 | 11/2006 | Viola et al. |
| 2007/0034669 A1 | 2/2007 | de la Torre et al. |
| 2007/0049953 A2 | 3/2007 | Shimoji et al. |
| 2007/0179528 A1 | 8/2007 | Soltz et al. |
| 2007/0203509 A1 | 8/2007 | Bettuchi |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |

FOREIGN PATENT DOCUMENTS

| | | |
|---|---|---|
| EP | 0 594 148 | 4/1994 |
| EP | 1 520 525 | 4/2005 |
| WO | WO 90/05489 | 5/1990 |
| WO | WO 98/17180 | 4/1998 |
| WO | WO 99/45849 | 9/1999 |
| WO | WO 03/082126 A1 | 10/2003 |
| WO | WO 03/105698 A2 | 12/2003 |
| WO | WO 03/105698 A2 * | 12/2003 |
| WO | WO 03/105968 | 12/2003 |
| WO | WO 2006/023578 | 3/2006 |

| | | |
|---|---|---|
| WO | WO 2006/044490 | 4/2006 |
| WO | WO 2006/083748 A1 | 8/2006 |

OTHER PUBLICATIONS

International Search Report from application PCT/US05/36740 mailed Mar. 23, 2007.

International Search Report from Application No. PCT/US2008/002981 dated Jun. 26, 2008.

International Search Report from Application No. EP 08 25 1779 dated Jul. 23, 2008.

* cited by examiner

HUB FOR POSITIONING ANNULAR STRUCTURE ON A SURGICAL DEVICE

BACKGROUND

1. Technical Field

The present disclosure relates to annular structures and devices for positioning the same and, more particularly, to hubs for positioning annular structures, gaskets and the like for use in conjunction with circular stapling devices, for reducing occurrences of leaking, bleeding and/or stricture.

2. Background of Related Art

Staples have traditionally been used to replace suturing when joining or anastomosing various body structures, such as, for example, the bowel or bronchus. The surgical stapling devices employed to apply these staples are generally designed to simultaneously cut and seal an extended segment of tissue in a patient, thus vastly reducing the time and risks of such procedures.

Linear or annular surgical stapling devices are employed by surgeons to sequentially or simultaneously apply one or more linear rows of surgical fasteners, e.g., staples or two-part fasteners, to body tissue for the purpose of joining segments of body tissue together and/or for the creation of anastomoses. Linear surgical stapling devices generally include a pair of jaws or finger-like structures between which body tissue to be joined is placed. When the surgical stapling device is actuated and/or "fired", firing bars move longitudinally and contact staple drive members in one of the jaws, and surgical staples are pushed through the body tissue and into/against an anvil in the opposite jaw thereby crimping the staples closed. A knife blade may be provided to cut between the rows/lines of staples. Examples of such surgical stapling devices are described in U.S. Pat. Nos. 4,354,628, 5,014,899 and 5,040,715, the entirety of each of which is incorporated herein by reference.

Annular surgical stapling devices generally include an annular staple cartridge assembly including a plurality of annular rows of staples, typically two, an anvil assembly operatively associated with the annular cartridge assembly, and an annular blade disposed internal of the rows of staples. Examples of such annular surgical stapling devices are described in U.S. Pat. Nos. 5,799,857 and 5,915,616 to Robertson et al., the entirety of each of which is incorporated herein by reference.

For most procedures, the use of bare staples, with the staples in direct contact with the patient's tissue, is generally acceptable. The integrity of the tissue will normally serve to prevent the staples from tearing out of the tissue and compromising the sealing before healing has occurred. However, in some surgical operations, surgical supports, e.g., meshes, are employed by surgeons to bridge, repair and/or reinforce tissue defects with a patient, especially those occurring in the abdominal wall, chest wall, diaphragm and other musculoaponeurotic areas of the body. Examples of surgical supports are disclosed in U.S. Pat. Nos. 3,054,406, 3,124,136, 4,347,847, 4,655,221, 4,838,884 and 5,002,551, the entirety of each of which is incorporated herein by reference.

When the staples are applied in surgical procedures utilizing surgical supports (i.e., reinforcing material), the legs of the staple typically pass from the cartridge jaw through a layer of the surgical support, and through the patient's tissue before encountering the anvil jaw. In an alternative procedure, the legs of the staple typically pass from the cartridge jaw through a first layer of the surgical support, then through the patient's tissue, and finally through a second layer of the surgical support before encountering the anvil jaw. With the staples in place, the stapled tissue is clamped between the layers of the surgical support.

The surgical supports described above are used in conjunction with linear surgical stapling devices. An end-to-end anastomosis stapler such as a Model "EEA™" instrument is available from United States Surgical, a Division of Tyco Health-Care Group, LP, Norwalk, Conn. and disclosed in U.S. Pat. No. 5,392,979 to Green et al. In general, an end-to-end anastomosis stapler typically places an array of staples into the approximated sections of a patient's bowel or other tubular organs. The resulting anastomosis contains an inverted section of bowel which contains numerous "B" shaped staples to maintain a secure connection between the approximated sections of bowel.

In addition to the use of surgical staples, biological tissue adhesives have been developed for tissue repair and the creation of anastomoses. Generally, biological adhesives bond separated tissues together to aid in the healing process and to enhance the tissue strength. Such adhesives may be used instead of suturing and stapling, for example, in surgical procedures, for the repair of tissue or the creation of anastomoses.

In addition to the use of biological adhesives, following the formation of the anastomosis, a separate instrument or device is used to apply biological sealants to the anastomosis. Typically, in a separate step, the biological sealants are applied to the outer surface of the anastomosis by spraying on, brushing on, swabbing on, any combinations thereof, or any other method contemplated by those skilled in the art. The biological sealants act to reduce and/or stop the incidents of leakage from the anastomosis.

One possible side effect of any end-to-end bowel anastomosis is its tendency to stenos over time, which stenosis can decrease the diameter of the lumen over time. Accordingly, the need exists for a structure which assists in maintaining the lumen of the anastomosed bowel or other tubular organ open over time.

The application of a suitable biocompatible adhesive offers many advantages to the patient and the surgeon alike, such as, for example, the possible reduction in the number of staples used, immediate sealing of the tissue being treated, a strengthening of the anastomosis, and a reduction in the occurrence of bleeding from the blood vessels, leakage through the tissue joint, and stricture. Moreover, use of biocompatible adhesives tends to minimize foreign body reaction and scarring.

Accordingly, the need exists for devices for properly positioning a structure with respect to opposed tissue which has been transected.

SUMMARY

The present disclosure relates to hubs for positioning annular structures, gaskets and the like on delivery devices, for reducing occurrences of leaking, bleeding, stricture and other complications.

According to an aspect of the present disclosure, an apparatus for forming an anastomosis between adjacent intestinal sections is provided. The apparatus includes an anastomosis device including an anvil assembly having a shaft which is selectively attachable to a tubular body portion; and a hub for locating an annular structure between the adjacent intestinal sections. The hub includes a central sleeve defining a lumen for receiving the shaft of the anvil assembly therein. The central sleeve forms a connection portion for engaging a feature on the anastomosis device and connecting the hub to the device. The apparatus further includes an annular structure operatively connected to the sleeve and extending radially outwardly therefrom.

According to another aspect of the present disclosure, an assembly for disposing an annular structure between adjacent intestinal sections is provided. The assembly includes an annular surgical stapling device, having an anvil assembly and a tubular body portion, the anvil assembly having an anvil member and an anvil shaft, the tubular body portion carrying a plurality of surgical staples in an annular configuration, the tubular body portion having a connection member disposed radially inward of the surgical staples, the anvil shaft of the anvil member being attachable to the connection member of the tubular body. The assembly further includes a hub including a central sleeve defining a lumen therethrough for selectively receiving the anvil shaft therein, and an annular structure radially extending from the central sleeve, wherein when the center hub is positioned on the anvil shaft the annular structure is concentrically located with respect to a longitudinal axis of the anvil shaft.

According to yet another aspect of the present disclosure, a method of disposing an annular structure between adjacent tissue sections is provided. The method includes the steps of: a) providing a surgical stapling device including an anvil assembly and a body portion, the anvil assembly including an anvil member supported on an anvil shaft and the body portion carrying a plurality of surgical staples and a knife; b) providing a hub for locating an annular structure between the adjacent tissue sections, the hub including a central sleeve defining a lumen which is configured and adapted for selectively receiving the shaft of the anvil assembly therein, and an annular structure operatively connected to the central sleeve and extending radially outwardly therefrom; c) inserting the anvil assembly into a first tissue section; and d) positioning the hub onto the anvil shaft such that the annular structure is concentrically located with respect to a longitudinal axis of the anvil shaft and such that the annular structure is positioned adjacent to the first tissue section.

The method further includes the steps of: a) inserting the body portion in a second tissue section; b) approximating the anvil assembly and body portion with one another so that an end portion of the first tissue section, an end portion of the second tissue section and the annular structure are disposed between the anvil member and the body portion, wherein the annular structure is disposed between the first tissue section and the second tissue section; c) deploying the staples from the body portion; and d) cutting the first tissue section, the second tissue section, and the annular structure with the knife.

The hub may include an annular flange monolithically formed with and extending from the central sleeve. The flange may extend from a first end of the central sleeve.

The central sleeve may include a plurality of longitudinally extending slots formed around a periphery thereof. Each elongate slot may extend through one end of the central sleeve. The slots may be defined by a plurality of flexible fingers.

The annular structure may be fabricated from at least one of a bioabsorbable and a non-bioabsorbable material. It is envisioned that the annular structure may include a material selected from the group consisting of an adhesive, a sealant, a hemostat, and a medicament.

The annular structure may include an outer annular disc defining a central opening having a dimension larger than an outer diameter of the central sleeve, and a web interconnecting the disc to the central sleeve.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein.

DETAILED DESCRIPTION OF EMBODIMENTS

Figure 1:
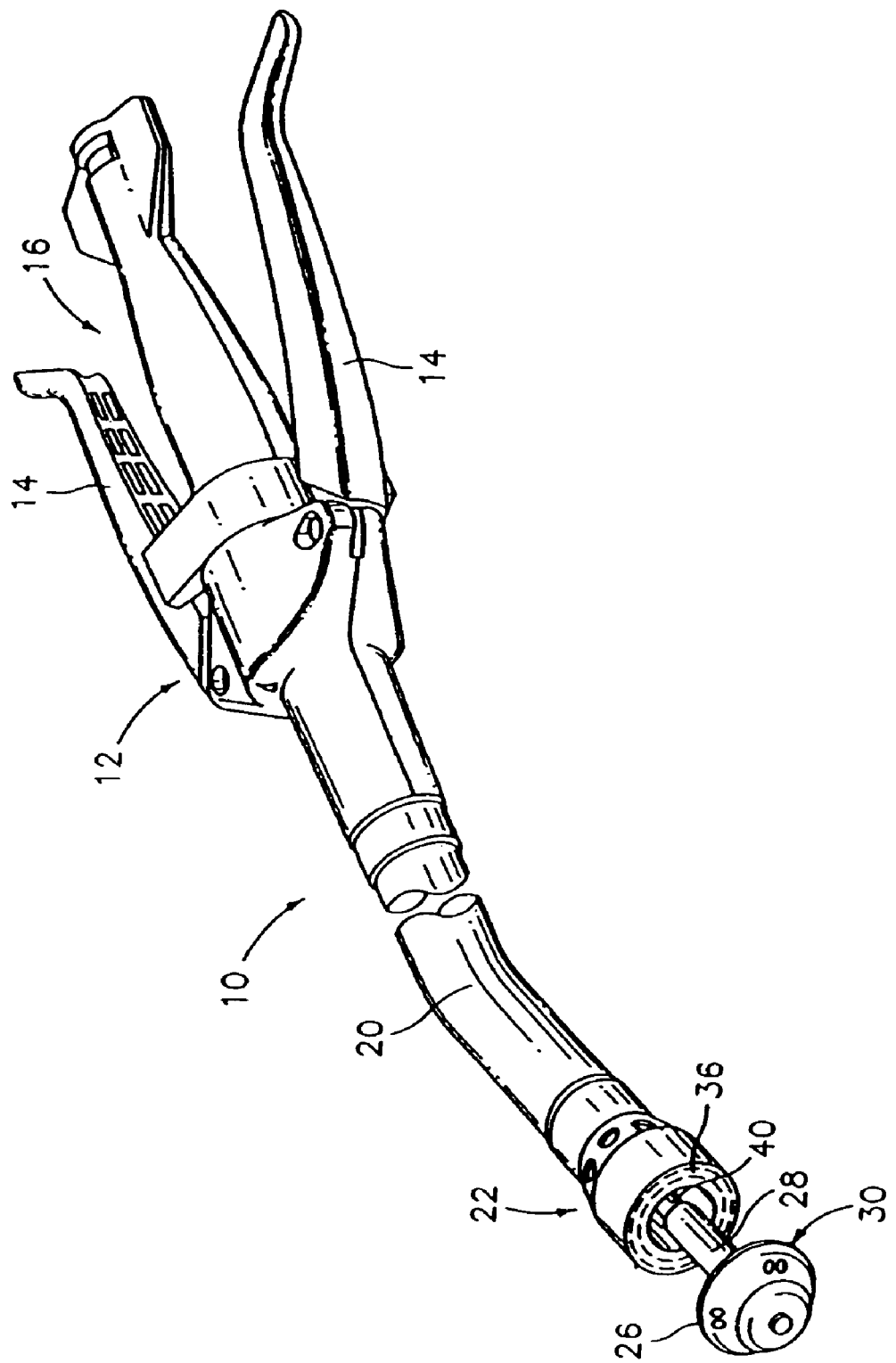
FIG. 1 is a perspective view of an exemplary annular surgical stapling device.

Embodiments of the presently disclosed center hub will now be described in detail with reference to the drawing figures wherein like reference numerals identify similar or identical elements. As used herein and as is traditional, the term "distal" refers to that portion which is furthest from the user while the term "proximal" refers to that portion which is closest to the user.

Referring initially to FIG. 1, an annular surgical stapling device, for use with the annular adhesive structures disclosed herein, is generally designated as 10. Surgical stapling device 10 includes a handle assembly 12 having at least one pivotable actuating handle member 14, and an advancing member 16. Extending from handle member 12, there is provided a tubular body portion 20 which may be constructed so as to have a curved shape along its length. Body portion 20 terminates in a staple cartridge assembly 22 which includes a pair of annular arrays of staple receiving slots 36 having a staple (not shown) disposed in each one of staple receiving slots 36. The body portion 20 includes a connection member 40 extending distally therefrom. An anvil assembly 30 has an anvil member 26 and an anvil rod 28 operatively associated therewith. The anvil rod 28 removably connects anvil assembly 30 to connection member 40 so that the anvil assembly 30 is positioned distally of staple cartridge assembly 22 of stapling device 10.

Staple cartridge assembly 22 may be fixedly connected to the distal end of tubular body portion 20 or may be configured to concentrically fit within the distal end of tubular body portion 20. Typically, staple cartridge assembly 22 includes a staple pusher (not shown) including a proximal portion having a generally frusto-conical shape and a distal portion defining two concentric rings of peripherally spaced fingers (not shown), each one of which is received within a respective staple receiving slot 36.

Typically, a knife (not shown), substantially in the form of an open cup with the rim thereof defining a knife edge, is disposed within staple cartridge assembly 22 and mounted to a distal surface of the staple pusher (not shown). The knife edge is disposed radially inward of the pair of annular arrays of staples. Accordingly, in use, as the staple pusher is advanced, the knife is also advanced axially outward.

Reference may be made to U.S. Pat. No. 5,915,616 to Viola et al., the entire content of which is incorporated herein by reference, for a detailed discussion of annular stapling device 10.

Figure 2:
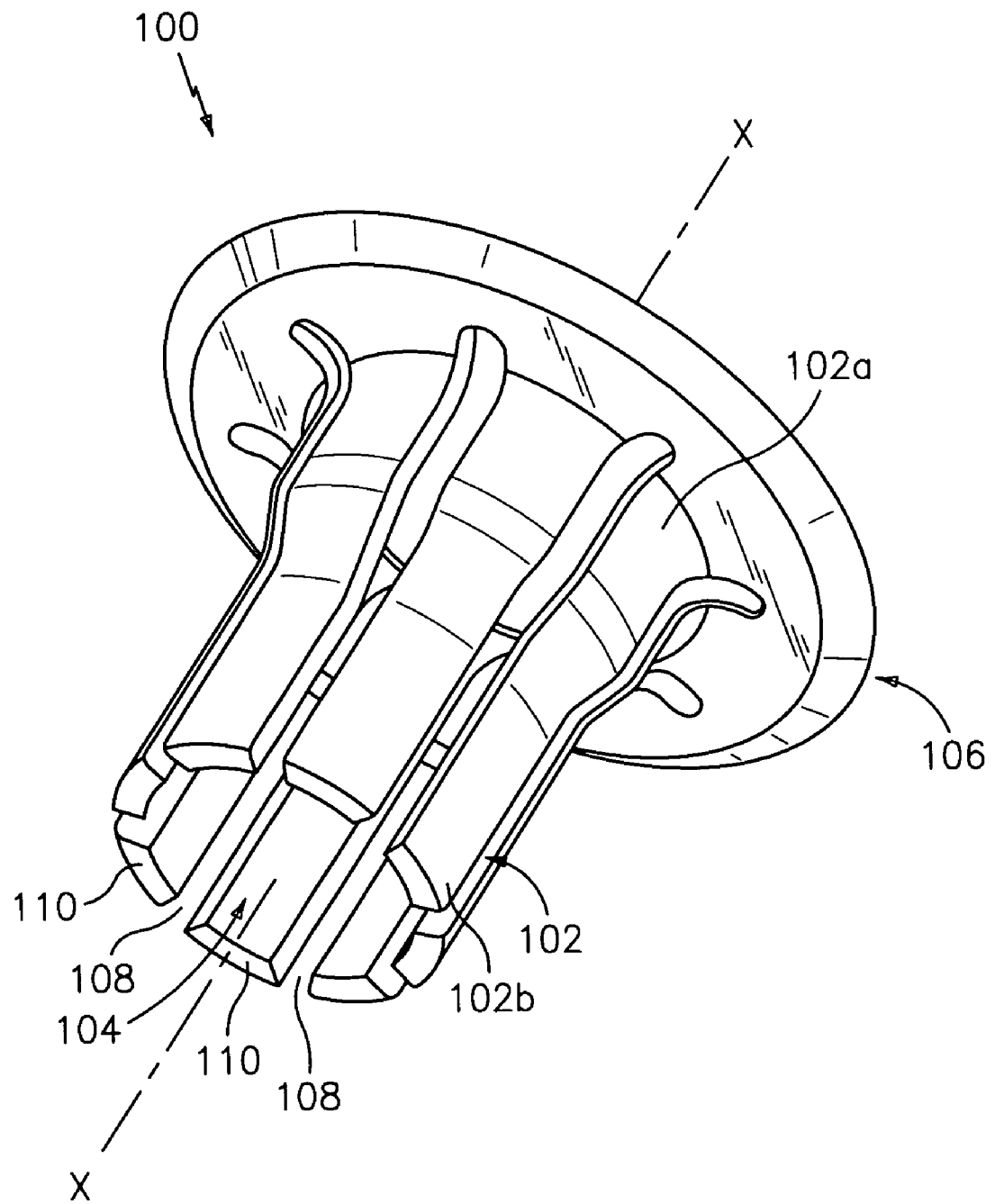
FIG. 2 is a perspective view of a hub according to an embodiment of the present disclosure for use with the surgical stapling device of FIG. 1.
Figure 3:
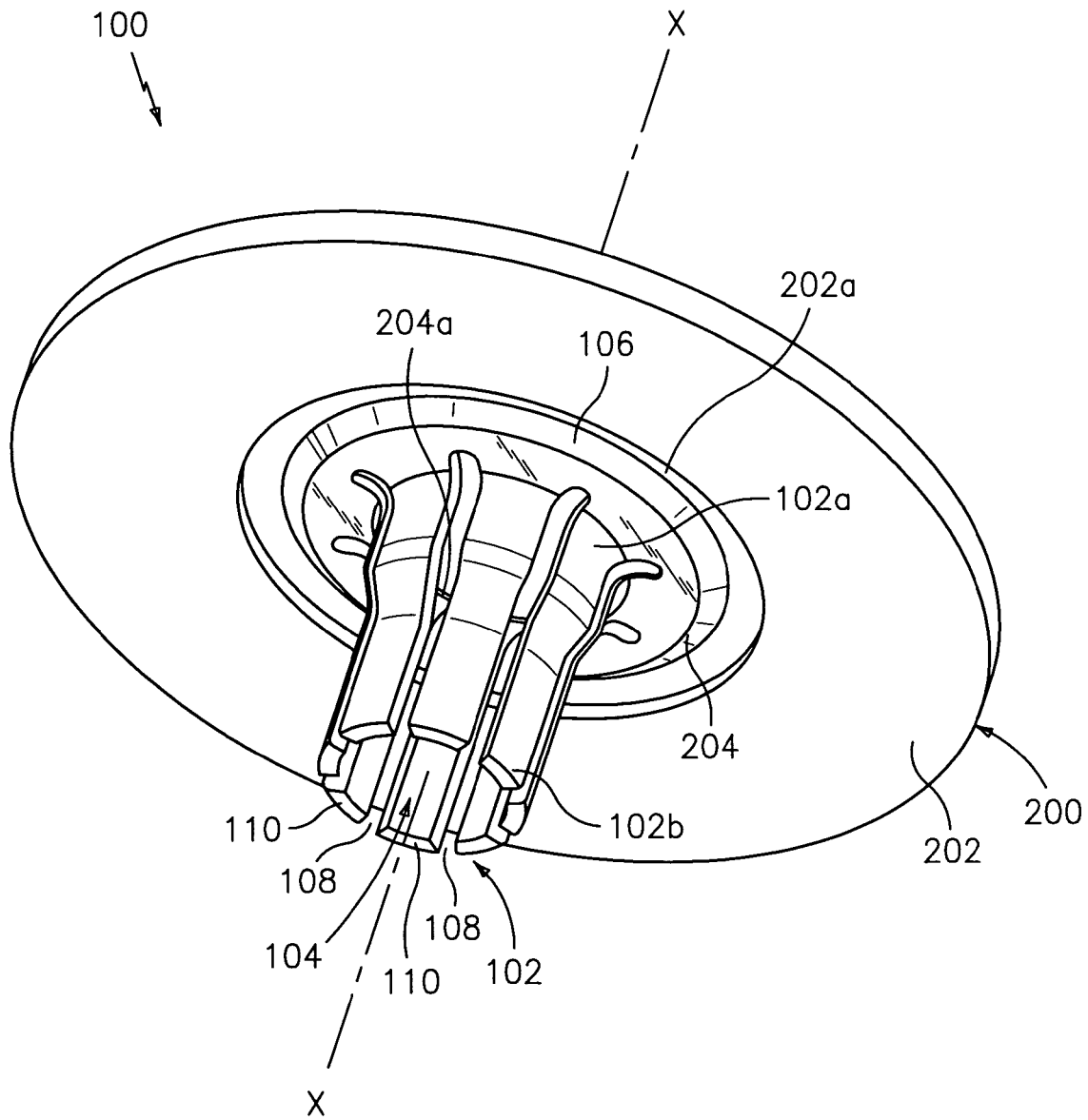
FIG. 3 is a perspective view of the hub of FIG. 2 including an annular structure operatively associated therewith.

Turning now to FIGS. 2 and 3, a hub 100, in accordance with an embodiment of the present disclosure, is shown and is described below. Hub 100 is intended to be used with stapling device 10, described above. Hub 100 is intended to locate and secure an annular structure 200 relative to anvil rod 28 of anvil assembly 30.

As seen in FIGS. 2 and 3, hub 100 includes a central sleeve 102 defining a central lumen 104 and a longitudinal axis "X". Hub 100 includes an annular flange 106 extending radially outwardly from a first end 102a of central sleeve 102. As seen in FIGS. 2 and 3, flange 106 may be orthogonally oriented with respect to the longitudinal "X" axis. Flange 106 is desirably monolithically formed with central sleeve 102. Central sleeve 102 is configured and dimensioned to selectively receive anvil rod 28 of anvil assembly 30 therethrough.

Central sleeve 102 forms a connection portion for connecting to the surgical stapling device 10. Central sleeve 102 includes a plurality of longitudinally oriented elongate slots 108 formed therethrough. In an embodiment, each elongate slot 108 extends though a second end 102b of central sleeve 102. Elongate slots 108 define a plurality of fingers 110 therebetween. As seen in FIGS. 2 and 3, each elongate slot 108 may extend through first end 102a of central sleeve 102. In this manner, each finger 110 is flexible and/or deflectable either radially inward or radially outward.

Hub 100 may be fabricated from a material suitably rigid so as to accurately locate hub 100 relative to anvil shaft 28 of anvil assembly 30 and suitably flexible so as to enable fingers 110 to deflect as needed, in the manner described above. Additionally, hub 100 may be fabricated from a material suitable for ethylene oxide (EtO) and/or gamma sterilization. Hub 100 may be fabricated from, and is not limited to, acrylonitrile butadiene styrene (ABS), glass filled polypropylene or some combination thereof. It is envisioned that hub 100 may be plastic injection molded or manufactured from any other suitable method known by one having skill in the art, such as, for example, machining, stamping and/or the like.

With particular reference to FIG. 3, hub 100 is shown having an annular structure 200 operatively associated therewith. Annular structure 200 includes an outer circular disc 202 defining a central opening 202a and a web 204 extending radially inward of central opening 202a of disc 202 and terminating in opening 204a. In an embodiment, central opening 202a has a dimension which is larger than an outer diameter of flange 106 of hub 100. As seen in FIG. 3, web 204 may extend from disc 202 to flange 106 of hub 100.

In an embodiment, disc 202 of annular structure 200 is sized such that an outer edge 202b thereof extends radially outward beyond staple retaining pockets 36 of staple cartridge assembly 22. Additionally, disc 202 of annular structure 200 is sized such that opening 204a is sized such that disc 202 extends radially inward beyond staple retaining pockets 36 of staple cartridge assembly 22.

It is contemplated that disc 202 of annular structure 200 may be fabricated from or include a surgical grade, biocompatible, non-absorbable (i.e., permanent) material; desirably a mesh impregnated with an adhesive, sealant and/or wound treatment material. For example, disc 202 may be fabricated from "TEFLON", which is a registered trademark owned by DuPont de Nemours & Co. It is further contemplated that disc 202 may be fabricated from a biocompatible polymeric foam, felt, polytetrafluoroethylene (ePTFE), gelatin, fabric or the like, or any other biocompatible material.

Non-absorbable materials used for disc 202 include, and are not limited to, those that are fabricated from such polymers as polyethylene, polypropylene, nylon, polyethylene terephthalate, polytetrafluoroethylene, polyvinylidene fluoride, and the like. Further non-absorbable materials include and are not limited to stainless steel, titanium and the like.

In one embodiment, disc 202 of annular structure 200 may be fabricated from a bio-absorbable material which is desirably impregnated with an adhesive, sealant, and/or other wound treatment material (e.g., a medicament). Accordingly, a sealant component of annular structure 200 can be used to retard any bleeding which may occur from the tissue, an adhesive component of annular structure 200 can be used to secure the approximated tissue together, and the bio-absorbability of annular structure 200 allows for annular structure 200 to be absorbed into the body after a predetermined amount of time. For example, annular structure 200 may remain in place in the body for approximately 2-3 weeks in order for the anastomosis to sufficiently heal prior to annular structure 200 being absorbed into the body. In other embodiments, annular structure 200 has at least one portion that is absorbable and at least one portion that is not absorbable.

Bio-absorbable materials used for disc 202 of annular structure 200 include, and are not limited to, those fabricated from homopolymers, copolymers or blends obtained from one or more monomers selected from the group consisting of glycolide, glycolic acid, lactide, lactic acid, p-dioxanone, α-caprolactone and trimethylene carbonate. Other bio-absorbable materials include and are not limited to, for example, Polyglycolic Acid (PGA) and Polylactic Acid (PLA). In one embodiment, disc 202 may be fabricated from bio-absorbable felt, ePTFE, gelatin or any other bio-absorbable materials.

It is contemplated that the adhesive is a biocompatible adhesive including, but not limited to, adhesives which cure upon tissue contact, which cure upon exposure to ultraviolet (UV) light, which are two-part systems which are kept isolated from one another and cure upon coming into contact with one another, which are pressure sensitive, which are any combinations thereof, or any other known suitable adhesive. In one embodiment, it is contemplated that an adhesive having a cure time of from about 10 to 15 seconds may be used. In another embodiment, it is contemplated that an adhesive having a cure time of about 30 seconds may be used.

It is envisioned that disc 202 of annular structure 200 may be impregnated with a pre-cured adhesive or sealant. The pre-cured sealant or adhesive will react with the moisture and/or heat of the body tissue to thereby activate the sealing and/or adhesive properties of the sealant or adhesive. It is envisioned that the pre-cured sealant or adhesive may be a hydro-gel or the like.

It is envisioned that the wound treatment material "W" includes and is not limited to one or a combination of adhesives, hemostats, sealants, coagulants, astringents, and medicaments. Other surgically biocompatible wound treatment materials "W" which may be employed in or applied by surgical instruments, including surgical staplers, include adhesives whose function is to attach or hold organs, tissues or structures; sealants to prevent fluid leakage; hemostats to halt or prevent bleeding; coagulants, astringents (e.g., sulfates of aluminum) and medicaments. Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials sold under the trade designations CoStasis™ by Tyco Healthcare Group, LP, and Tisseel™ sold by Baxter International, Inc.

The wound treatment material may include a cross-linking material and/or reactive agent that reacts with the annular structure, tissue or both. The resulting material acts as a seal or tissue-joining material that is non-absorbable. For example, the wound treatment material may be based on biocompatible cross-linked polymers formed from water soluble precursors having electrophilic and nucleophilic groups capable of reacting and cross-linking in situ, including those disclosed in U.S. Pat. No. 6,566,406, the entire contents of which are incorporated herein by reference.

The wound treatment material may be disposed on annular structure 200 or impregnated into annular structure 200. Medicaments may include one or more medically and/or surgically useful substances such as drugs, enzymes, growth factors, peptides, proteins, dyes, diagnostic agents or hemostasis agents, monoclonal antibodies, or any other pharmaceutical used in the prevention of stenosis.

Wound treatment material "W" may include visco-elastic film forming materials, cross-linking reactive agents, and energy curable adhesives. It is envisioned that wound treatment material "W", and in particular, adhesive may be cured with the application of water and/or glycerin (e.g., 1,2,3-pranatetriol, also known as glycerol and glycerine) thereto. In this manner, the water and/or glycerin cure the adhesive and hydrate the wound.

It is further contemplated that wound treatment material "W" may include, for example, compositions and/or compounds which accelerate or beneficially modify the healing process when particles of the composition and/or compound are applied to or exposed to a surgical repair site. For example, the wound treatment material "W" may be a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, wound treatment material "W" may include one or several growth promoting factors, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

In one embodiment, it is contemplated that disc 202 of annular structure 200 may be impregnated with a first component of a two-part adhesive and that the device deploys the second component of the two-part adhesive. For example, in a surgical stapler 10, the staples, which are retained in staple receiving slots 36 of staple cartridge assembly 22, may be coated with a second component (e.g., a reactant) of the two-part adhesive. In this manner, the first component of the adhesive is activated when the staples penetrate and capture disc 202 of annular structure 200 during the firing sequence of surgical stapling device 10, and the two components of the adhesive contact one another.

It is further envisioned that annular structure 200 may include a single layered disc 202 including a homogeneous array of bio-absorbable or non-absorbable materials or a heterogeneous array of bio-absorbable and/or non-absorbable materials. In certain embodiments, disc 202 may be impregnated with a pressure sensitive adhesive which is activated when adjacent layers of tissue are approximated, with disc 202 disposed therebetween.

In an alternate embodiment, it is contemplated that annular structure 200 may include a layered body portion having at least two layers. In this embodiment, each layer may include a homogeneous or heterogeneous array of bio-absorbable and/or non-absorbable materials. It is envisioned that each layer may be separated from one another prior to the surgical procedure. In certain embodiments, the annular structure 200 includes the structures disclosed in U.S. patent application Ser. Nos. 11/241,267 and 11/248,846, the disclosures of which are hereby incorporated by reference herein in their entirety.

With continued reference to FIG. 3, web 204 may be fabricated from any suitable mesh or the like. As seen in FIG. 3, web 204 of annular structure 200 is secured to flange 106 of hub 100 in such a manner that disc 202 is concentric with central sleeve 102 and with the longitudinal "X" axis.

Figure 4:
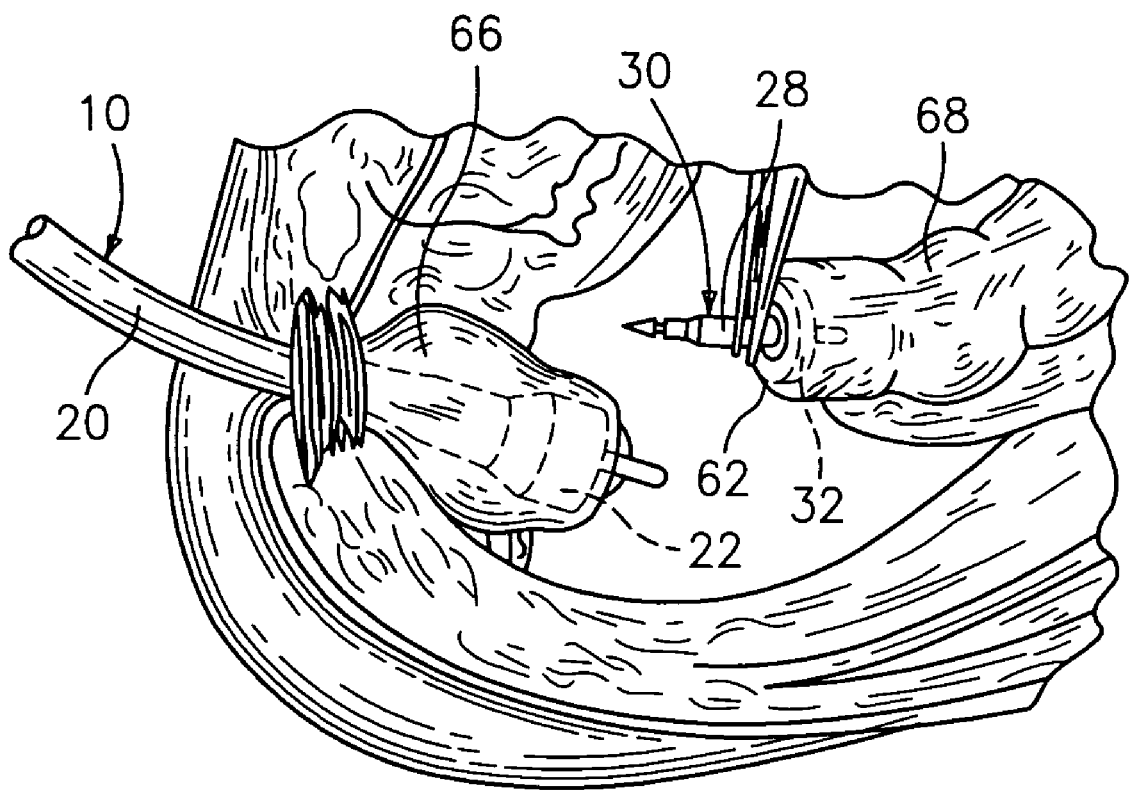
FIG. 4 is a perspective view of the intestinal area of a patient, illustrating a method of using the annular surgical stapling device of FIG. 1.
Figure 5:
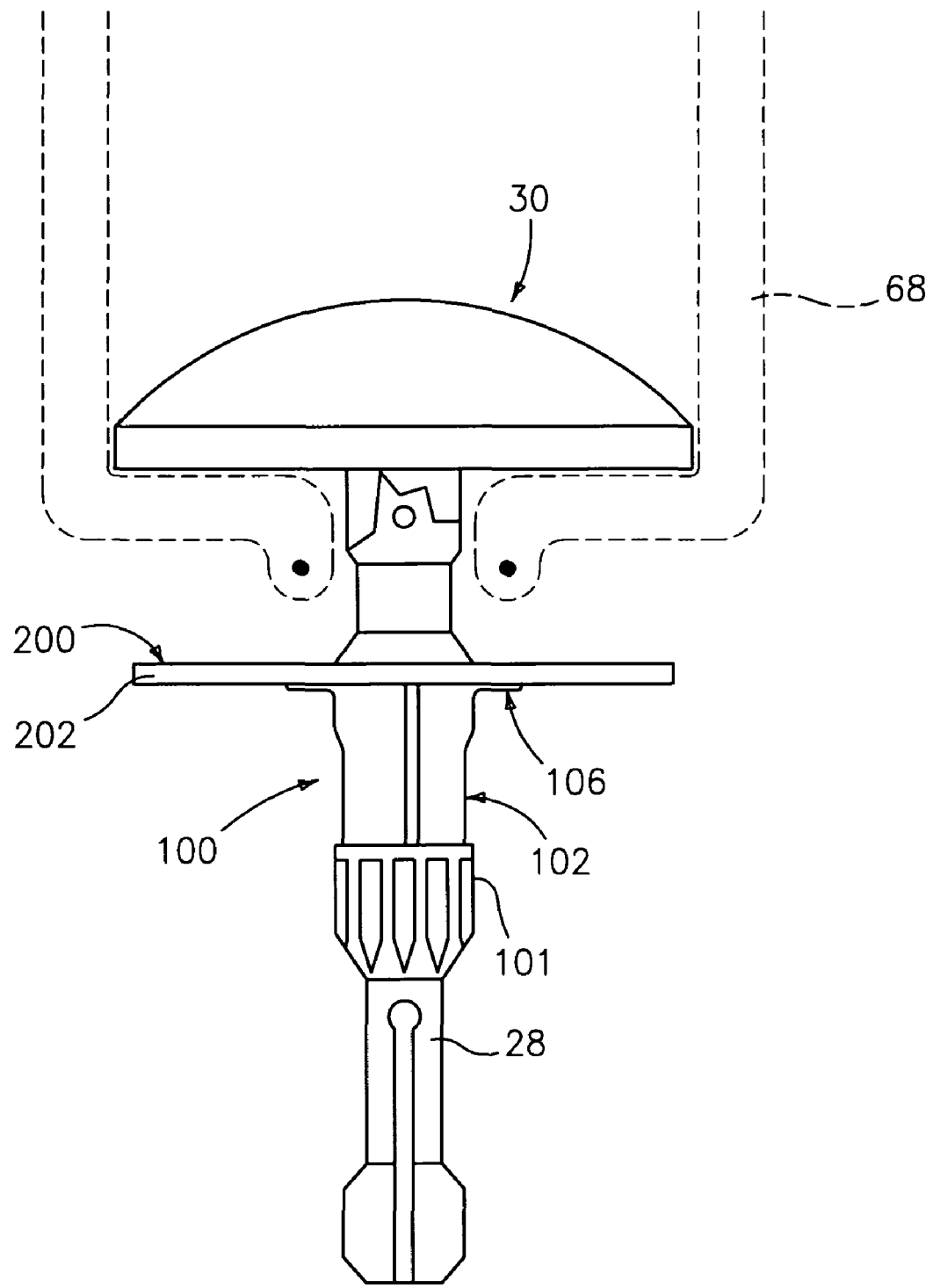
FIG. 5 is an enlarged side elevational view of the anvil assembly of FIG. 4, illustrating the hub of FIG. 3 positioned on the anvil rod thereof.

Turning now to FIGS. 4 and 5, there is illustrated the use of surgical stapling device 10 and hub 100 in an anastomosis procedure to effect joining of intestinal sections 66 and 68. The anastomosis procedure is typically performed using minimally invasive surgical techniques including laparoscopic means and instrumentation. At the point in the procedure shown in FIG. 4, a diseased intestinal section has been previously removed, anvil assembly 30 has been introduced to the operative site either through a surgical incision or trans-anally and positioned within intestinal section 68, and tubular body portion 20 of surgical stapling device 10 has been inserted trans-anally into intestinal section 66. Intestinal sections 66 and 68 are also shown temporarily secured about their respective components (e.g., shaft 28 of anvil assembly 30, and the distal end of tubular body portion 20) by conventional means such as a purse string suture "P".

As seen in FIG. 5, hub 100 is attached onto shaft 28 of anvil assembly 30, prior to the coupling of anvil assembly 30 to the distal end of tubular body portion 20, and either before or after the anvil assembly is secured to intestinal section 68. In particular, shaft 28 of anvil assembly 30 is inserted through first end 102a of central sleeve 102 into lumen 104 of central sleeve 102. In this position, annular structure 200 is located adjacent intestinal section 68. Following positioning of hub 100 onto shaft 28 of anvil assembly 30, the surgeon maneuvers anvil assembly 30 until the proximal end of shaft 28 is connected to connection member 40 of surgical stapling device 10, wherein the mounting structure (not shown) engages shaft 28 to effect the connection. As shown in FIG. 5, the shaft 28 of the anvil assembly 30 has a feature, such as a protrusion or recess or flange 101, for engagement by hub 100. The fingers 110 are desirably flexible to assist the hub 100 and annular structure 200 onto shaft 28. In other embodiments, a shaft associated with the body portion 20 has a feature for engagement by the hub 100.

Thereafter, while ensuring disc 202 of annular structure 200 is extending radially outward, anvil assembly 30 and tubular body portion 20 are approximated to approximate intestinal sections 66, 68 and capture disc 202 of annular structure 200 therebetween. With disc 202 of annular structure 200 captured between intestinal sections 66, 68, surgical stapling device 10 may be fired thereby stapling intestinal sections 66, 68 to one another, securing disc 202 of annular structure 200 between intestinal section 66, 68, and cutting the portion of tissue and annular structure 200 disposed radially inward of the knife, to complete the anastomosis.

Hub 100 is removed from the surgical site upon withdrawal of surgical stapling device 10 from the surgical site. The hub 100 locates the annular structure 200 on the surgical stapling device 10 so that it is positioned at the desired location with respect to the portions of tissue being joined. The procedure is simplified in that the annular structure 200 may not need to be positioned on shaft 28 inside the patient's body.

It will be understood that various modifications may be made to the embodiments of the presently disclosed surgical stapling apparatus and the various dispensing systems and methods described above. For example, the hub and annular structure may be used on a surgical device for positioning the annular structure, that does not deploy staples. Such surgical devices may incorporate a wound treatment material dispensing apparatus. Therefore, the above description should not be construed as limiting, but merely as exemplifications of preferred embodiments. Those skilled in the art will envision other modifications within the scope and spirit of the present disclosure.

What is claimed is:

1. An assembly for disposing an annular structure between adjacent intestinal sections, the assembly comprising:
   a) an annular surgical stapling device having an anvil assembly and a tubular body portion, the anvil assembly having an anvil member and an anvil shaft, the tubular body portion carrying a plurality of surgical staples in an annular configuration, the tubular body portion having a connection member disposed radially inward of the surgical staples, the anvil shaft of the anvil member including a flange and being attachable to the connection member of the tubular body portion; and
   b) a hub adapted for support on the anvil shaft to engage the flange of the anvil shaft, the hub including a central sleeve defining a lumen therethrough for selectively receiving the anvil shaft therein, and an annular structure radially extending from the central sleeve, the annular structure including an outer annular disc defining a central opening having a dimension larger than an outer diameter of the central sleeve and a web interconnecting the disc to the central sleeve, wherein the central sleeve comprises at least one resilient finger extending substantially in a longitudinal direction, and wherein, when the hub is supported on the anvil shaft, the at least one resilient finger engages the flange of the anvil shaft to position the annular structure at a location spaced a distance from a tissue contacting surface of each of the anvil assembly and the tubular body portion.

2. The assembly according to claim 1, wherein the hub includes an annular flange monolithically formed with and extending from the central sleeve.

3. The assembly according to claim 2, wherein the annular flange extends from a first end of the central sleeve.

4. The assembly according to claim 1, wherein the central sleeve includes a plurality of longitudinally extending slots formed around a periphery thereof.

5. The assembly according to claim 4, wherein each elongate slot extends through one end of the central sleeve, the slots being defined by.

6. The assembly according to claim 1, wherein the annular structure is fabricated from at least one of a bioabsorbable and a non-bioabsorbable material.

7. The assembly according to claim 6, wherein the annular structure comprises a material selected from the group consisting of an adhesive, a sealant, a hemostat, and a medicament.

* * * * *